US010060862B2

(12) United States Patent
Cui et al.

(10) Patent No.: US 10,060,862 B2
(45) Date of Patent: Aug. 28, 2018

(54) MICROWAVE IMPEDANCE MICROSCOPY USING A TUNING FORK

(71) Applicants: Yongtao Cui, Riverside, CA (US); Yue Ma, Stanford, CA (US); Zhixun Shen, Stanford, CA (US)

(72) Inventors: Yongtao Cui, Riverside, CA (US); Yue Ma, Stanford, CA (US); Zhixun Shen, Stanford, CA (US)

(73) Assignee: Board of Trustees of the Leland Stanford Junior Univers, Stanford, CA (US)

( * ) Notice: Subject to any disclaimer, the term of this patent is extended or adjusted under 35 U.S.C. 154(b) by 25 days.

(21) Appl. No.: 15/479,657

(22) Filed: Apr. 5, 2017

(65) Prior Publication Data

US 2017/0299525 A1    Oct. 19, 2017

Related U.S. Application Data

(60) Provisional application No. 62/324,331, filed on Apr. 18, 2016.

(51) Int. Cl.
*G01N 22/00* (2006.01)
*G01N 27/02* (2006.01)
(Continued)

(52) U.S. Cl.
CPC ............. *G01N 22/00* (2013.01); *G01N 27/02* (2013.01); *G01Q 10/045* (2013.01); *G01Q 20/04* (2013.01); *G01Q 60/30* (2013.01)

(58) Field of Classification Search
CPC ......... G01N 27/02; G01Q 60/30; G01Q 20/04
See application file for complete search history.

(56) References Cited

U.S. PATENT DOCUMENTS 8,266,718 B2 *   9/2012   Lai .......................... B82Y 35/00
                                                     850/21
8,307,461 B2    11/2012   Li et al.
(Continued)

OTHER PUBLICATIONS

International Search Report, PCT/US2017/026312, dated Jul. 18, 2017.
im et al., "Distance control for a near-field scanning microwave microscope in liquid using a quartz tuning fork," pplied Physics Letters, vol. 86, p. 153506 (2005).
Oliva et al., "Electrochemical preparation of tungsten tips for a scanning tunneling microscope," Review of Scientific Instruments, vol. 67, p. 1917 (1996).
(Continued)

*Primary Examiner* — Jermele M Hollington
*Assistant Examiner* — Alvaro Fortich
(74) *Attorney, Agent, or Firm* — Charles S. Guenzer

(57) ABSTRACT

A microwave impedance microscope including a tuning fork having a high-aspect ratio etched metal tip electrode extending transversely to one tine of the fork and having a high aspect ratio to thereby reduce parasitic capacitance. The metal tip may be electrochemically etched from a wire, then bonded to the tine. The fork is slightly inclined from the surface of the sample and the tip electrode projects transversely to the fork. A microwave signal is impressed on the tip. Microwave circuitry receives microwave signals reflected from the sample back into the tip and demodulates the reflected signal according to the impressed signal. Further circuitry further demodulates the reflected signal according to the lower-frequency signal causing the fork to oscillate at its mechanically resonant frequency. A multi-wavelength matching circuit interposed between the microwave circuitry and the probe includes a coaxial cable of length half a fundamental microwave wavelength.

20 Claims, 3 Drawing Sheets

(51) Int. Cl.
*G01Q 10/04* (2010.01)
*G01Q 20/04* (2010.01)
*G01Q 60/30* (2010.01)

(56) References Cited

U.S. PATENT DOCUMENTS

| | | |
|---|---|---|
| 2005/0246129 A1 | 1/2005 | Lee et al. |
| 2006/0087381 A1* | 4/2006 | Johnson ............... H01P 1/262 333/22 R |
| 2006/0152232 A1 | 7/2006 | Shvets et al. |
| 2010/0045306 A1 | 3/2010 | Ookubo |
| 2010/0299791 A1 | 11/2010 | Lee et al. |
| 2014/0090118 A1* | 3/2014 | Weber-Bargioni .... G01Q 60/22 850/32 |
| 2015/0028210 A1 | 1/2015 | Han et al. |

OTHER PUBLICATIONS

Kim et al., "Tip-sample distance control for near-field scanning microwave microscopes," Review of Scientific Instruments, vol. 74, p. 3675 (2003).

Kim et al., "Distance control for a near-field scanning microwave microscope in liquid using a quartz tuning fork," Review of Scientific Instruments, vol. 86, p. 153506 (2005).

Cui et al., "Quartz tuning fork based microwave impedance microscopy," Review of Scientific Instruments, vol. 98, p. 063711 (Jun. 28, 2016).

* cited by examiner

MICROWAVE IMPEDANCE MICROSCOPY USING A TUNING FORK

RELATED APPLICATION

This application claims benefit of provisional application U.S. 62/324,331, filed Apr. 18, 2016 and incorporated herein by reference.

GOVERNMENT INTEREST

This invention was made partially with government support under grant PHY-0830228 awarded by the National Science Foundation. The government has certain rights in the invention.

FIELD OF THE INVENTION

The invention relates generally to material measurement systems. In particular, the invention relates to microwave impedance microscopy.

BACKGROUND ART

Electrical measurement systems and techniques have long been used to characterize the electrical properties of bulk materials, for example, resistivity, permittivity and permeability. These techniques have been adapted to measure characteristics of surfaces and thin films and have been combined with optical techniques for measuring further properties such as semiconductor type and concentrations and chemical bonding. Attempts to apply these electrical and optical techniques to the fine surface structures developed in semiconductor integrated circuits (ICs) have been stymied by the small scale of modern IC features, typically well below 100 nm, with the result that most measurement probes and beams average over neighboring features of the IC.

Atomic force microscopy has been developed to profile the topography of a specimen with a resolution of 10 nm and less. In a usual implementation, an atomic force microscope (AFM) includes a mechanical probe with a tip positioned at the end of a flexible cantilever. The tip is tapered to have an apex having a diameter of, for example, less than 50 or 100 nm though 5 nm is currently achievable. The sharp tip may be realized either through anisotropic etching of crystalline silicon to form sharp pyramidal tips with dimensions of a few silicon crystalline spacings or by etching a metal wire to form a conical tip. Through atomic interactions between the tip and specimen sufficient to affect the cantilever flexing, the probe tip can be made to hover a small fixed distance above the specimen as the tip is scanned over the specimen. Thereby, the specimen surface can be profiled by such a mechanical AFM with vertical and horizontal resolutions on the order of nanometers.

As described by Lai et al. in U.S. Pat. No. 8,266,718, incorporated herein by reference, atomic force microscopy has been combined with microwave measurement techniques to implement microwave impedance microscopy, which incorporates a microwave probe into the AFM cantilever tip. A conventional AFM system automatically scans the microwave tip closely adjacent a sample surface so that microwave circuitry can electrically characterize small areas of the sample and thus image the electrical characteristics of the scanned surface. Li et al. describe an improved microwave probe tip in U.S. Pat. No. 8,307,461. PrimeNano, Inc. of Santa Clara, Calif. markets the ScanWave™ module for AFMs to provide high-resolution imaging of permittivity and conductivity of materials at the nanoscale. The cantilever of this microwave impedance microscope includes both the tip and a shielded microwave strip line. The shielding reduces parasitic capacitance and thus enables measurement of very small electrical signals. The probe can be manufactured by techniques similar to those used for semiconductor integrated circuits, but these techniques are complex and should be performed in an expensive clean room.

In an alternative form of atomic force microscopy, a tuning fork substitutes for the vibrating cantilever. Instead, a probe tip is positioned at the end of one of the tongs of the fork. An oscillatory signal is applied to pair of electrodes formed on the parallel tongs to cause them to vibrate or oscillate against each other, preferably at the mechanically resonant frequency of the fork. Kim et al., in "Tip-sample distance control for near-field scanning microwave microscopes," *Review of Scientific Instruments*, vol. 74, p. 3675 (2003), describe a microwave microscope having an etched tungsten probe electrode tip mounted longitudinally on the tips of one fork tine to utilize shear-force displacement. The shift of the mechanical resonance of the fork is used to track the topography of the sample and control the height of the probe tip. Kim et al. make no mention of their tuning fork improving the electrical measurements characterizing their sample or measuring electrical parameters of the sample.

SUMMARY OF THE INVENTION

In one aspect of the invention, a microwave impedance microscopy system includes a tuning fork on which a metallic probe stylus is bonded to one tine of the fork and oscillates vertically on the tine toward and away from a sample. Advantageously, the stylus has a probe tip tapered to form a concave cone about a tip axis and having an aspect ratio of at least three and preferably at least five. Conveniently, the probe tip is formed from a thin wire bonded to the tine and extending away from it while free standing to its bonding to a microwave transmission line such as a coaxial cable. Preferably, the fork is inclined at a small angle with respect to the sample surface with the probe tip extending perpendicularly to the sample surface.

In another aspect of the invention, two tines of the tuning fork are formed with electrodes to which an oscillatory signal is applied. Electrical circuitry connected to the probe tip receives microwave signals from the probe tip and demodulates it according to the oscillatory signal vibrating the fork, preferably after demodulating it according to the applied microwave signal.

In a further aspect of the invention, an impedance matching circuit coupling microwave circuitry to the probe tip includes a microwave transmission line of length resonant at a fundamental frequency and with its harmonics of multiple microwave signals generated by a microwave source in the microwave circuitry. The microwave circuitry may further include a microwave demodulator, such as a mixing circuit, demodulating the generated microwave signal with a microwave signal impressed upon the probe tip.

DETAILED DESCRIPTION OF THE PREFERRED EMBODIMENTS

Figure 1:
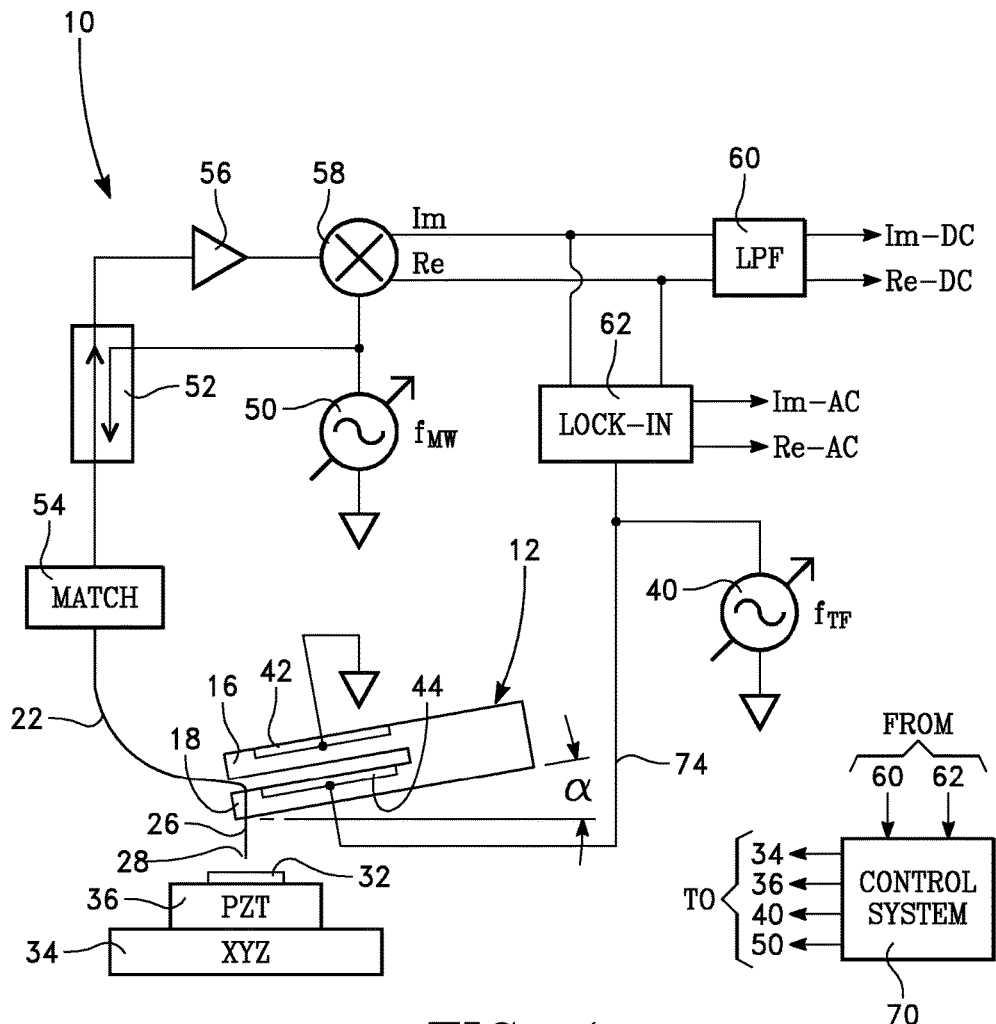
FIG. 1 is a block diagram of a microwave impedance microscope system of the invention.
Figure 2:
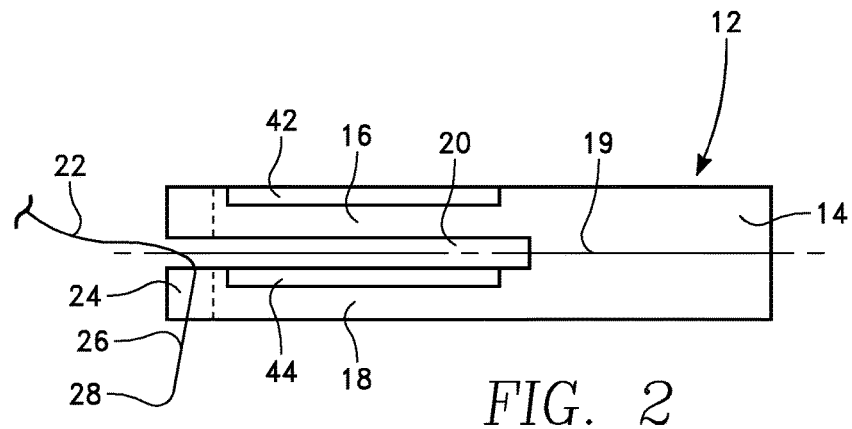
FIG. 2 is an enlarged side view of a tuning fork usable with the invention.

FIG. 1 illustrates an embodiment of a microwave impedance microscope system 10 based on a tuning fork 12, which may be formed from a single member, preferably of an insulating material such as quartz. The tuning fork 12, illustrated in larger scale in FIG. 2, includes a base 14 from which two parallel arms or tines 16, 18, alternatively called prongs, extend parallel to a fork axis 19 with a gap 20 therebetween. Quartz tuning forks are widely available in the watch industry complete with their electrodes, leads and contact pads. Other materials could be used but quartz is insulating and has a high quality factor. One usable tuning fork is model ABT38-32,768KHZ available from Abracon of Irvine, Calif. and having an overall length of somewhat less than 1 cm. To form the probe, a round metal wire 22 is bonded to a distal end of the lower one of the tines 18 in a adhesive area 24 applied to both of the tines 16, 18 sufficient to fix the wire 22 to the lower tine 18. The bonded wire 22 extends below the lower tine 18 to form a stylus 26 having a sharp probe tip 28. This description is referenced to the orientation of FIG. 1 but other orientations are possible.

Figure 3:
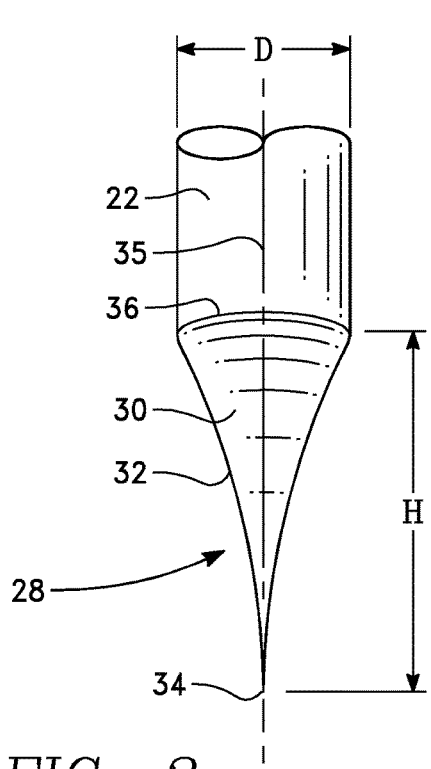
FIG. 3 is a side view at a small oblique angle of a conical probe tip etched from a metal wire.

The sharpened probe tip 28, as illustrated in the slightly upwardly oblique side view of FIG. 3, may be electrochemically etched from the end of the metal wire 22 to form a probe tip cone 30 having concave sides 32 and terminating in an apex 34, all aligned about an axis 35 extending from the distal end of the wire 22. In practice, the cone 30 is not perfectly conical buts its conical shape is apparent in normal viewing. The metal wire 22 is electrically conductive and may be made of platinum, iridium/tungsten, gold or other metals preferably not subject to surface oxidation. It is also thin, preferably less than 40 μm in diameter D, and more preferably no more than 25 μm so as to minimize its flexural rigidity; however, excessively thin wires 22 would increase the probe impedance. Sides 32 of the cone 30 are concave and produce a very small apex 34, for example, having a diameter of 50 nm. The concave cone 30 has a height H from its apex 34 to a rim 36 of the unetched wire 22 of diameter D to thereby produce an aspect ratio AR=H/D for the probe tip 28. For a wire diameter of 25 μm or less, the aspect ratio is at least 5 although aspect ratios AR of greater than 3 provide many of the beneficial results to be described later. The probe tip 28 can be sharpened by, prior to bonding to the fork 12, electrochemically etching the end of the wire 22 in a process described by Oliva et al., *Review of Scientific Instruments*, vol. 67, p. 1917 (1996). A tip diameter of no more than 50 nm is easily obtained. Smaller tip diameters can be achieved with more elaborate electrical controls of the electrochemical etching.

Returning to FIG. 1, the tuning fork 12 is positioned and fixedly supported above a sample 32 to be measured, but the axis 19 of the tuning fork 12 is inclined at a small angle α from the contact point at the surface of the sample 32, for example at less than 25° and preferably no more than 15° but greater than 5°. The small inclination provides clearance between the sample 32 and the rest of the tuning fork 12 while causing the probe tip 28 to move primarily in the direction perpendicular to the fork axis 19. The wire stylus 26 extends from adjacent the fork's lower corner along the tip axis 35 approximately perpendicular to the surface of the sample 32. That is, the wire 22 is bonded to the adhesive area 24 with its tip axis 35 inclined at an angle slightly offset at the angle α from the perpendicular to the fork axis 19, that is, within 25° of the normal to the supporting surface. The stylus 26 preferably extends about 200 μm below the lower tine 18.

The sample 32 is mounted on a support surface of an XYZ stage 34 providing x-y scanning and rough vertical positioning in the z direction and a PZT transducer tube 36 providing fine positional control in the z direction approximately along the axis 35 of the probe stylus 26. Positional support and control by the XYZ stage 34 and PZT transducer tube 36 may be transferred wholly or partially to support and move the base 14 of the fork 12.

A low-frequency oscillator 40 operating at a tuning fork frequency $f_{TF}$ applies its oscillatory signal across two opposed linear electrodes 42, 44 attached respectively to the two tines 16, 18 to cause them to be alternately attracted together and repelled apart. The amplitude of the oscillatory signal determines the mutual mechanical deflection of the tines 16, 18. The oscillator 40 is preferably tunable to match the mechanical resonant frequency of the tines 16, 18 of the tuning fork 12. The tuning fork frequency $f_{TF}$ is generally within a range of 10 to 100 kHz. One freshly prepared fork had a resonant frequency of 32,768 Hz, which shifted somewhat after glueing the wire 22 to the fork 12. The tuning fork 12 had a high quality factor Q of, for example, about 3000 in air and it may be increased to 100,000 in vacuum and at cryogenic temperatures. The oscillator 40 circuitry is only schematically illustrated in FIG. 1 and the oscillator circuitry may advantageously incorporate controllable amplification and feedback tuning as the resonant frequency drifts or otherwise changes.

A microwave oscillator 50 is connected through a directional coupler 52 and a match circuit 54 to the wire 22 terminating in the probe tip 28 to thereby irradiate a near-field microwave signal upon the sample 32. The microwave oscillator 50 outputs a microwave signal at a microwave frequency $f_{MW}$, for example, between 100 MHz and 50 GHz although a more commonly used range is 1 GHz to 10 GHz. The interaction of the probe tip 28 with the sample 32 causes a microwave signal to be reflected back, at least partially at the microwave frequency $f_{MW}$, into the probe tip 28 and back through the match circuit 54 into the directional coupler 52, which separates out the reflected signal and directs it through an amplifier 56 to a microwave mixer 58.

The match circuit 54 matches the impedance of the microwave transmission line used in microwave circuitry with the much larger impedance of the bare wire 22 and its probe tip 28 to thereby increase the coupling efficiency and reduce reflections. An advantageous embodiment of a match circuit 54' is illustrated in the microwave schematic of FIG. 4. A small series matching capacitor 60 of capacitance $C_{match}$ couples the center conductor of a 50Ω coaxial cable 62 used in the microwave circuitry with the center conductor of a resonant 50Ω coaxial cable 64 of resonant length. That is, the 50Ω coaxial cable 62 has a length L of λ/2 that is one-half the wavelength of the microwave radiation on the transmission line 54 so that it exhibits a fundamental resonance at the microwave frequency $f_{MW}$ as well as higher-order harmonics $nf_{MW}$. For a microwave frequency of 1 GHz, the resonant cable length L of typical coaxial cable is about 10 cm. The matching capacitance $C_{match}$ is small, approximately 0.2 pF and is chosen to such that its impedance $1/2\pi f_{TF} C_{match}$ is much larger than the 50Ω characteristic impedance of the coaxial cable 62, for example, by a factor of at least 10. The surrounding coaxial shields are grounded. Other types of microwave transmission lines may be substituted for the coaxial cables. The probe wire 22 is free-standing between the tine 18 and the body to which the coaxial cable 64 is fixed. The thin free-standing portion of the wire 22 is soldered at its proximal end to the center conductor of the coaxial cable 64, which acts as a support member and is much more rigid than the free-standing wire 22 to thereby decrease the mechanical coupling of the vibrating tine 18 from the rest of the microwave circuitry. The probe wire 22 and its probe tip 28 have a self-capacitance 66 with a value $C_{tip}$ small enough that its impedance is again much larger than the characteristic impedance of the microwave transmission line.

Returning to FIG. 1, the microwave mixer 58 mixes the microwave signal from the microwave source 52, which is proportional to the microwave signal incident on the sample 32 through the probe tip 28, with the microwave signal reflected from the probe tip 28 and the sample 32 to thereby demodulate the reflected signal according to the incident microwave signal. The mixer 58 acts as a homodyne detector which compares the received or reflected signal with a reference incident signal at the same frequency. The mixer 58 outputs two signals representative of the real and imaginary parts Re and Im of the reflected signals, that is, the in-phase and out-of-phase components. A dual low-pass filter 60 having a cutoff below the tuning fork frequency $f_{TF}$, for example at 1 kHz, removes the oscillatory components arising from the vibrations of the tuning fork 12 to produce DC components Re-DC and Im-DC of the Re and Im signals, and hence related to the admittance and capacitance (or conductivity and permittivity) of the portion of the sample 32 adjacent the apex 34 of the probe tip 28.

The microwave circuitry is designed to extract small variations of the tip-sample interactions, about 10 aF, but the high sensitivity renders the systems susceptible to small changes in the microwave circuit, such as temperature and cable contact. Most of this drift can be removed by measuring a differential signal using the tuning fork oscillation as a reference. A dual lock-in amplifier 62 receives the real and imaginary signals Re and Im from the mixer 58 and demodulates them with reference to the tuning fork frequency $f_{TF}$ to produce the amplitudes of the low-frequency real and imaginary signals Re-AC and Im-AC, which are much less sensitive to slow system drifts.

A control system 70 receives data for the DC components from the low-pass filter 60 and the AC components from the lock-in amplifier 62 both for internal control purposes and for data recording. It controls the XYZ stage 34 for scanning across the sample 32 and for rough vertical movement and it controls the PZT tube 36 for fine vertical movement. It may also be used to fine tune the tuning fork oscillator 40 and to scan the microwave oscillator 50 including harmonic hopping.

Figure 5:
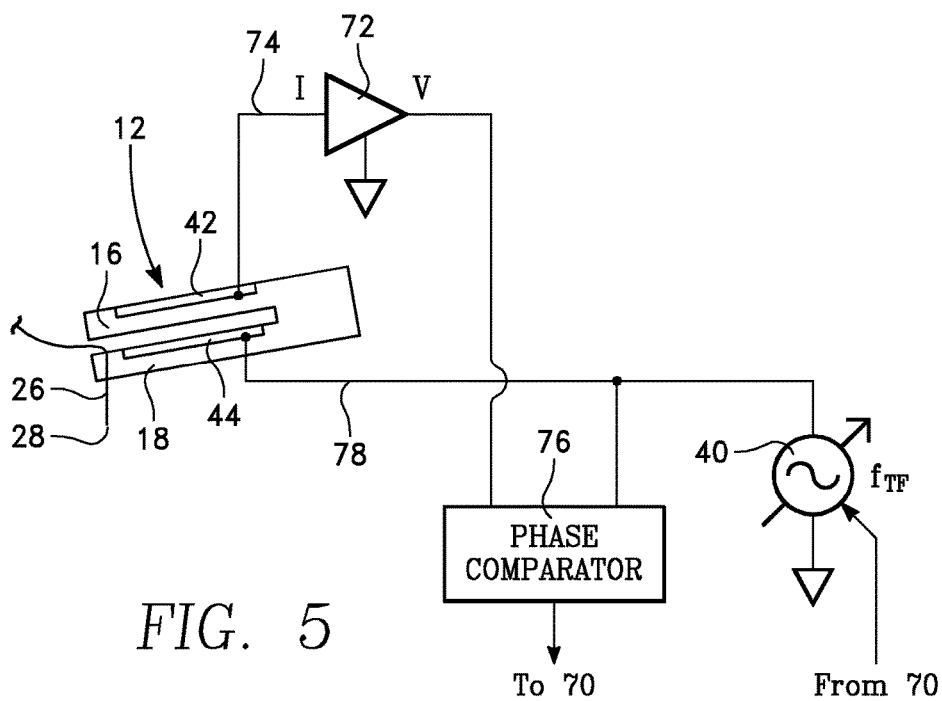
FIG. 5 is a functional circuit diagram of a phase-locked feedback loop used to control and measure the height of the probe above the sample.

As the probe tip 28 approaches and possibly contacts the sample 32, the fork's resonant frequency slightly changes and thus varies with the height of the probe tip 28 above the sample 32. A phase-locked loop can thereby be used to control the height of the probe tip 28 and to additionally monitor the topography of the sample 32. The functional schematic circuit illustrated in FIG. 5 illustrates such a phase-locked loop. An AC signal from the tuning fork oscillator 40 at the frequency $f_{TF}$ excites the oscillation of the tines 16, 18 of the tuning fork 12, producing an AC current into and out of tine electrodes 42, 44 at the same frequency $f_{TF}$. For the tuning fork resonator, as in any resonator, the relative phase between the driving AC voltage and the response AC current is a fixed value at resonance. In the loop circuit, a transimpedance amplifier 72 detects the AC current on a ground line 74 from the counter electrode 42. The transimpedance amplifier 72 acts as both a current sensor or current-to-voltage converter and a ground and may be implemented with an operational amplifier with negative feedback as is well known and described in "Transimpedance amplifier" on the Wikipedia website. A phase comparator 76 compares the phase of the detected current with the phase of the voltage signal on a supply line 78 from the oscillator 40 (or an unillustrated amplifier) and applied to the driving electrode 44 of the tuning fork 12 as the microwave circuitry applies and detects microwave signals through the probe tip 28 and other circuitry. The lines 74, 78 and the capacitor created by the two electrodes 42, 44 form the low-frequency oscillating circuit through the tuning fork 12.

The control system 70 receives the differential phase detected by the phase comparator 76. If it has changed from its resonant value, that is, the predetermined phase difference, the control system 70 adjusts the tuning fork oscillator 40 to change the tuning fork frequency $f_{TF}$ to bring the tuning fork 12 back into resonance as determined by the predetermined phase difference. By tracking the frequency $f_{TF}$ as the distance between the probe and the sample is decreased, the system can determine at which height during the fork oscillation the probe tip 28 has made contact with the sample 32 or even has significantly interacted with it through van der Waal's forces. Thereby, the probe tip 28 can be kept oscillating at a constant distance above the sample 32. Thus, not only can the probe height be controlled for consistent impedance measurements, but the microwave probe tip can be used for topographic profiling. Other electrical phase-loop feedback circuits may link the phase comparator 76 and the low-frequency oscillator 40 to effect the non-optical height control of the probe tip 28.

Much of the microwave, detection and control circuitry can be implemented with commercial microwave network analyzers, such as Agilent 8753ES. A commercial scanning probe microscope controller, such as Nanonis SC5 with OC4, can be used for phase-locked loop frequency tracking and feedback, as well as for scanning and data acquisition.

An advantage of the tuning fork in microwave impedance microscopy is that as the tip oscillates toward and away from the sample surface, the distance oscillation changes the impedance between the tip and the sample and thus allows the Im-AC and Re-AC signals to be extracted. In the vertical orientation of the Kim et al. paper, the tip moves roughly parallel to the sample surface so that the tip-sample distance does not change and the microwave impedance is not modulated by the tuning fork.

Figure 6:
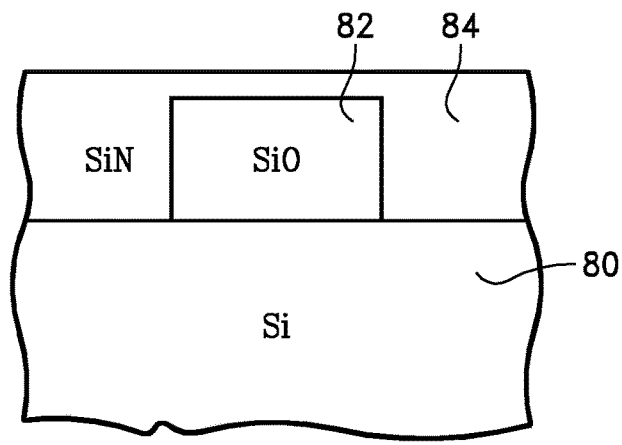
FIG. 6 is a cross-sectional view of a test sample probed by an embodiment of the microwave impedance microscope of the invention in comparison to other microscopes.

The invention has been tested on several microstructures for comparison to simple topographic scanning and to microwave impedance microscopy using a shielded cantilever probe. One such sample structure, shown in cross-section in FIG. 6, includes a silicon substrate 80 on which was deposited and patterned a square 82 of $SiO_2$ having a dielectric constant $\in$ of 3.9 and formed with lateral sides of about 4 μm and a thickness of 90 nm. An overlayer 84 of $Si_3N_4$ having a dielectric constant $\in$ of 7 was deposited and planarized to thicknesses of 120 nm over the silicon substrate 80 and of approximately 30 nm over the buried $SiO_2$ square 82. As a result, the generally flat surface was mostly distinguishable only by the difference of the dielectric constants of the buried silicon oxide square 82 and the silicon nitride overlayer 84. With topographic detection, the buried square 82 was barely detectable either with a pyramidal silicon probe tip or with the etched probe tip on the tuning fork of the invention. With the conventional pyramidal probe tip on the shielded cantilever, the buried square 82 was clearly visible in the microwave Im-DC signal. With the etched probe tip fixed on the tuning fork and a fork oscillation amplitude of about 2 nm, the Im-DC signal produced a somewhat fuzzy outline but the Im-AC signal produced an outline comparable to that produced by the shielded cantilever probe.

Thus, the simple tuning fork probe of the invention with little shielding provides microwave impedance microscopy of quality nearly equaling that obtained with a complicated and more expensive shielded strip line probe. It is believed that the geometry of the etched metal probe tip significantly reduces the parasitic capacitance between the probe and the sample. As stated before, the narrow etched metal probe tip 28 shown in FIG. 3 has a high aspect ratio AR of about 5 and the wire 22 supporting it from above is relatively narrow, for example, less than 40 μm and preferably no more than 25 μm so that the effective area of the wire forming an electrode for parasitic capacitance is small. The thinness of the wire 22 makes it very flexible and reduces the damping imposed on the vibrating tuning fork 12 to which it is attached on its mid portion. In contrast, the typical shielded probe tip of the prior art relies on an anisotropically etched silicon tip with its apex angle determined by the silicon crystallography. As a result, its aspect ratio AR is fixed at about 0.8. Also, the etch metal probe tip 28 of the invention may be relatively long, for example, 100 μm, while in some embodiments an anisotropically etched silicon tip vertically extends only about 5 μm before it widens out for its horizontal electrical lines. As a result, an unshielded probe tip 28 and connecting wire 22 allowed by the invention suffer parasitic capacitance no worse than that of the shielded probe and cantilever of the prior art.

Figure 4:
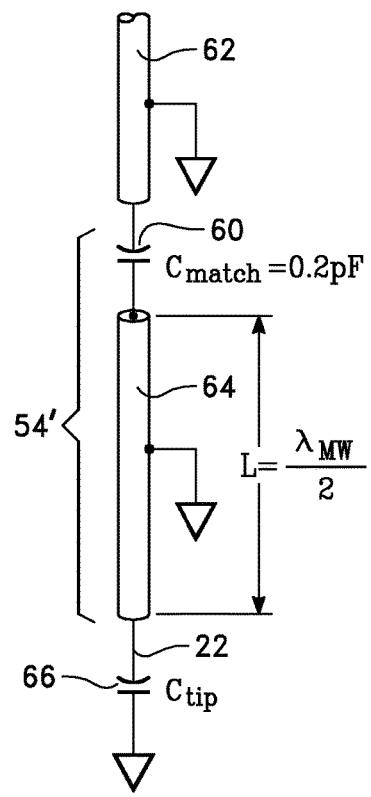
FIG. 4 is an electrical schematic of a resonant matching circuit.

Microwave impedance microscopy benefits when the frequency of the microwave signal can be varied between different measurements, for example, when the electronic response of the sample being probed has a strong frequency dependence over the microwave range. The match circuit 54 of FIG. 1 presents a challenge since most conventional matching circuits, especially for matching to layered strip line, require significant adjustments of their electrical components to afford matching over large frequency variations. However, the resonant matching circuit 54' of FIG. 4 provides effective matching not only at the fundamental match resonance at the microwave frequency $f_{MW}=c_T/2L$, where L is the length of the resonant transmission line 64 and $c_T$ is the speed of propagation of an electrical signal on that transmission line, but also at higher-order resonances or harmonics at microwave frequencies $f_{MW}=nc_T/2L$, where n is an integer greater than 1 for the harmonics.

Figure 7:
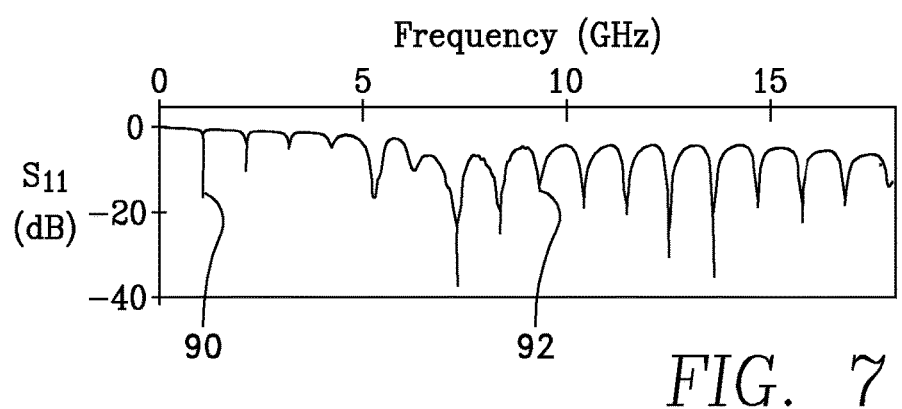
FIG. 7 is a spectrum of the microwave reflectivity of the tuning fork probe of FIG. 1 over a range of microwave frequencies applied to the probe.

The microwave reflection coefficient $S_{11}$ of the tuning fork sensor of FIG. 1 was measured over the frequency range 300 kHz to 18 GHz. As shown in the spectrum of FIG. 7, microwave power was effectively matched to the probe at not only the fundamental frequency of 1 GHz of the match circuit 54' of FIG. 4 but also at or near its harmonics.

In another experiment, the microscope system 10 of FIG. 1 scanned a sample 32 having a 4 μm-wide and 15 nm-thick surface-oxidized aluminum square patterned on a 2 μm-thick $SiO_2$ layer over a silicon substrate. The fork oscillation was set to 2 nm and the microwave source 50 was set on two runs respectively at 1 GHz, corresponding to the primary resonance 90 of FIG. 7, and at 9.3 GHz, corresponding to the ninth-order resonance 92. Both the Im-DC and Im-AC images showed little variation between the two microwave frequencies, demonstrating not only the lack of frequency dependence in the sample but also the operability of the system at two widely different microwave frequencies. The microscope system 10 could be tuned to other resonances of FIG. 7 to provide a finer grain spectrum not only of images but of numerical values of admittance and capacitance of the probed structure.

Cui et al. have described this invention in "Quartz tuning fork based microwave impedance microscopy," *Review of Scientific Instruments*, vol. 87, p. 063711 (2016) and in the parent provisional application, which should be consulted for more experimental results and a more complete listing of the prior art.

Although the described embodiment inclines the tuning fork to be nearly horizontal to the sample surface, the invention is not so limited. The tuning fork 12 of FIGS. 1 and 2 may be vertically oriented with its axis 19 aligned within a deviation of 25° to be perpendicular to the surface of the sample 32 and its support 19 and the wire 22 glued to the tine 18 to so that its probe tip 26 extends within a deviation of 25° perpendicularly to the sample surface. A vertical orientation of the tuning fork with the probe tip being generally parallel to the tine 18 as it vibrates may enhance the sensitivity of measuring spatial inhomogeneities of dielectric function in the sample.

The invention thus includes a microwave impedance microscope providing high-quality microscopy with a simple and inexpensive probe and also providing for multi-frequency microwave microscopy. The tuning fork microwave impedance microscope of the invention allows a true topographic scan of the sample in either a cryogenic environment or in a strong magnetic field. Since the height may be controlled by electrically monitoring the tuning fork's resonant frequency, the inventive microscope also enables impedance microscopy without introducing any light in the vicinity of sensitive samples.

What is claimed is:

1. A microwave impedance microscope, comprising:
   a support having a support surface for supporting a sample to be tested;
   a tuning fork which has two tines extending parallel to a fork axis with a gap there between and being caused to vibrate with respect to the fork axis in response to an oscillatory signal applied thereto;
   a probe electrode formed from a metal member having a tapered probe tip extending parallel to a probe axis generally perpendicular to the support surface for a height H between a rim and an apex of the tapered probe tip and having an aspect ratio AR of at least 3 between the height H and a rim diameter DR of the rim, wherein at least a portion of the metal member including the tapered probe tip is fixed to one of the two tines and projects to the sample along the probe axis; and
   microwave circuitry for impressing an incident microwave signal to the tapered probe tip, for receiving a reflected microwave signal from an interaction of the incident microwave signal with the sample, and for producing at least one output signal representing an electrical characteristic of the sample.

2. The microscope of claim 1, wherein the microwave circuitry demodulates the reflected microwave signal according to the incident microwave signal.

3. The microscope of claim 2, wherein the microwave circuitry includes a mixer demodulating the reflected microwave signal according to the incident microwave signal.

4. The microscope of claim 1, further comprising a demodulating circuit demodulating the at least one output signal according to the oscillatory signal.

5. The microscope of claim 1, further comprising:
a microwave source capable of producing the incident microwave signal at a fundamental microwave frequency and at least one harmonic frequency thereof; and
a matching circuit disposed between the microwave circuitry and the probe electrode that is resonant at the fundamental microwave frequency and at the at least one harmonic frequency.

6. The microscope of claim 5, wherein the matching circuit includes a microwave transmission line having a length equal to one-half a wavelength of the fundamental microwave frequency on the microwave transmission line and a capacitor connected in series between the microwave circuitry and the microwave transmission line.

7. The microscope of claim 6, wherein the capacitor has an impedance at the fundamental microwave frequency greater than a characteristic impedance of the microwave transmission line.

8. The microscope of claim 1, wherein the tuning fork is aligned with the fork axis extending from its distal end upwardly at no more than 25° from a plane parallel to the support surface.

9. The microscope of claim 1, wherein the tapered probe tip is aligned with the probe axis extending at no more than 25° from a normal to a plane parallel to the support surface.

10. The microscope of claim 1, wherein the tapered probe tip has a concave conical shape and is formed from a distal end of a wire forming the metal member and having a wire diameter DW away from the tapered probe tip of no more than 40 im, wherein the rim forms a boundary between a non-tapered portion of the wire and the tapered probe tip and wherein the wire is bonded to the one of the two tines.

11. The microscope of claim 10, wherein a middle portion of the wire is bonded to the one of the two tines and a proximal end of the wire is fixed to a support member supporting a transmission line to the microwave circuitry and wherein the wire is free standing between the middle portion and the proximal end.

12. The microscope of claim 10, wherein the wire diameter DW is no more than 25 μm.

13. A microwave impedance microscope, comprising:
a probe having an electrode probe tip extending towards a sample to be tested; microwave circuitry for impressing an incident microwave signal to the electrode probe tip, for receiving a reflected microwave signal from an interaction of the incident microwave signal with the sample, and for producing at least one output signal representing an electrical characteristic of the sample, the microwave circuitry including a microwave source capable of producing the incident microwave signal at a fundamental microwave frequency and at least one harmonic frequency thereof; and
a matching circuit disposed between the microwave circuitry and the probe electrode probe tip and that is resonant at the fundamental microwave frequency and at the at least one harmonic frequency.

14. The microscope of claim 13, wherein the matching circuit includes a microwave transmission line having a length equal to one-half a wavelength of the fundamental microwave frequency and a capacitor connected in series between the microwave circuitry and the microwave transmission line and having an impedance at least ten times greater than a characteristic impedance of the microwave transmission line.

15. The microscope of claim 13, further comprising a tuning fork which has two tines extending parallel to a fork axis with a gap there between, having the probe tip fixed to one of the two tines at a distal end of the fork, and being caused to vibrate with respect to the fork axis in response to an oscillatory signal applied thereto and wherein the fork axis extends from the distal end of the fork upwardly at no more than 25° from a plane parallel to a support surface of a support supporting the sample.

16. The microscope of claim 13, further comprising a tuning fork which has two tines extending parallel to a fork axis with a gap there between and being caused to vibrate with respect to the fork axis in response to an oscillatory signal applied thereto and wherein the electrode probe tip extends along a probe axis extending at no more than 25° from a plane perpendicular to a support surface of a support supporting the sample.

17. A microwave impedance microscope, comprising:
a support having a support surface for supporting a sample to be tested;
a tuning fork which has two tines extending parallel to a fork axis with a gap there between and being caused to vibrate with respect to the fork axis in response to an oscillatory signal applied thereto, wherein the fork axis extends from distal ends of the two tines upwardly at no more than 25° from a plane parallel to the support surface;
a probe electrode having a probe tip extending parallel to a probe axis generally perpendicular to the support surface and fixed to one of the tines and projects along the probe axis to the sample; and
microwave circuitry for impressing an incident microwave signal to the probe tip, for receiving a reflected microwave signal from an interaction of the incident microwave signal with the sample, and for producing at least one output signal representing an electrical characteristic of the sample.

18. The microscope of claim 17, wherein the probe tip is formed from a metal member, is conically shaped for a height H between a rim and an apex of the probe tip, and has an aspect ratio AR of at least 3 between the height H and a rim diameter D of the rim.

19. The microscope of claim 17, wherein the probe tip is formed from a metal member comprising a metal wire having a wire diameter of no more than 40 μm.

20. The microwave impedance microscope of claim 17, further comprising a demodulating circuit demodulating the at least one output signal according to the oscillatory signal.

* * * * *